(12) United States Patent
Boden et al.

(10) Patent No.: US 6,423,272 B1
(45) Date of Patent: Jul. 23, 2002

(54) FLUID SENSING DEVICE USING DISCOTIC LIQUID CRYSTALS

(75) Inventors: Neville Boden, Leeds; Jonathan Clements, Mirfield; Bijan Movaghar, Leeds, all of (GB)

(73) Assignee: The University of Leeds, Leeds (GB)

(*) Notice: Subject to any disclaimer, the term of this patent is extended or adjusted under 35 U.S.C. 154(b) by 0 days.

(21) Appl. No.: 09/142,160

(22) PCT Filed: Mar. 3, 1997

(86) PCT No.: PCT/GB97/00572

§ 371 (c)(1),
(2), (4) Date: Sep. 2, 1998

(87) PCT Pub. No.: WO97/32202

PCT Pub. Date: Sep. 4, 1997

(30) Foreign Application Priority Data

Mar. 2, 1996 (GB) ............................................. 9604525

(51) Int. Cl.[7] ............................................. G07N 27/00
(52) U.S. Cl. ..................... 422/98; 73/31.05; 422/82.01; 422/82.02; 436/149; 436/150
(58) Field of Search .................. 422/98, 83, 82.01, 422/82.02; 436/149, 150; 252/299.01, 299.62; 428/1; 560/64, 80; 540/122; 514/259; 73/31.05

(56) References Cited

U.S. PATENT DOCUMENTS

| | | | |
|---|---|---|---|
| 5,282,381 A | | 2/1994 | Krone-Schmidt |
| 5,345,213 A | | 9/1994 | Semancik et al. |
| 5,370,820 A | * | 12/1994 | Boden et al. .......... 252/299.01 |
| 5,571,401 A | * | 11/1996 | Lewis et al. |
| 5,798,197 A | * | 8/1998 | Paulus et al. |

FOREIGN PATENT DOCUMENTS

| | | | |
|---|---|---|---|
| DE | WO 96/06144 | * | 2/1996 |
| GB | 2243917 | * | 11/1991 |
| WO | WO 94/29263 | | 12/1994 |

OTHER PUBLICATIONS

Arikain et al., Effects of side–chain length on the charge properties of discotic liquid crystals and their implications for the transport mechanism, J. Mater. Chem. 5(12), 2161–5, 1995.*
M. Van der Auweraer et al, Microchemistry 1994, 455–468.*
N. Boden et al, J. Am. Chem. Soc. 1994, 116, 10807–10808.*
E. O. Arikainen et al, J. Mater. Chem. 1995, 5, 2161–2165.*
L. Y Chiang et al, Mol. Cryst. Liq. Cryst. 1985, 125, 279–288.*
N. Boden et al, Chem. Phys. Lett. 1988, 152, 94–99.*
A. Wilson et al, Sens. Actuators, B 1991, 4, 499–504.*
P. Roisin et al, J. Mater. Chem. 1992, 2, 131–137.*
J. D. Wright Chem. Funct. Dyes, Proc. Int. Symp., 2nd 1993, 207–214.*
J. D. Wright et al, Sens. Actuators B 1993, 13, 276–280.*
N. Boden et al, J. Chem. Phys. 1993, 98, 5920–5931.*
H. Bottcher et al, J. Mater. Chem. 1993, 3, 1187–1197.*
J. D. Wright et al. Chem. Abstr. Oct. 1993, 119, 173105s.*
N. Boden et al, J. Mater. Sci.: Mater. Electron. Apr. 1994, 5, 83–88.*
M. J. Cook J. Mater. Sci.: Mater. Electron. Apr. 1994, 5, 117–128.*
J. D. Wright Chem. Abstr. May 1995, 122, 254829v.*

* cited by examiner

Primary Examiner—Arlen Soderquist
(74) Attorney, Agent, or Firm—Klauber & Jackson

(57) ABSTRACT

The present invention discloses a fluid sensing device comprising a substrate having at least one type of dicotic liquid crystals disposed therein and arranged to form an array of columnar structures and a contact means for measuring the flow of electric charge through the upper part of the columnar structure surface. Also disclosed is a method for detecting a fluid comprising the steps of: exposing a sensing device to a fluid so that the fluid interacts with the surface of the discotic liquid crystal; applying a voltage to the contact means; measuring a flow of electric charge; and, analyzing a variable current flow to identify the fluid.

18 Claims, 12 Drawing Sheets

$D_h$

HAT6
Crystal $\xrightarrow{67°C}$ $D_h$ $\xrightarrow{100°C}$ Liquid

HAT6-NO₂ 293K

FIG. 12
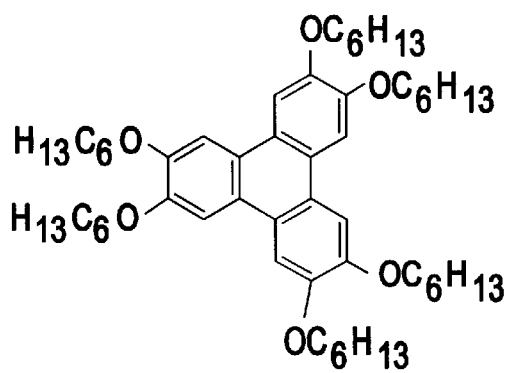
2,3,6,7,10,11 - Hexa(hexyloxy) triphenylene (HAT6)
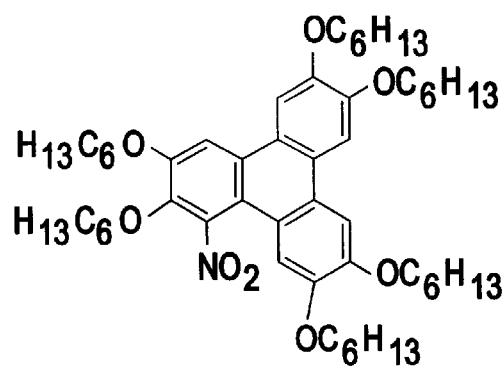
1-Nitro 2,3,6,7,10,11 - Hexa(hexyloxy) triphenylene (HAT6-NO$_2$)
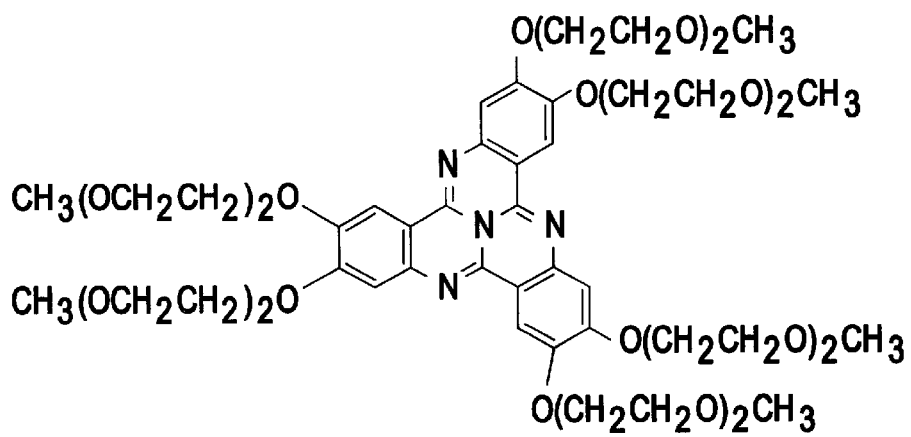
2,3,7,8,12,13 - Hexa-[2-(2'-MethoxyEthoxy)-Ethoxy]TriCycloQuinazoline (HMEETCQ)

1,4,8,11,15,18,22,25 - Octa-(Octyl)Phthalocyanine (PC8)

FIG. 14

| Compound | Example | Phase Behavior |
|---|---|---|
| HATn | HAT6 | K 67°C $D_h$ 100°C I |
| HATn-X | HAT6-$NO_2$ | K <RT $D_h$ 136°C I |
| HXETCQ | HMEETCQ | K 77°C $D_h$ 233°C I |
| PCn | PC8 | K 83°C $D_h$ 159°C I |

FLUID SENSING DEVICE USING DISCOTIC LIQUID CRYSTALS

BACKGROUND OF THE INVENTION

1. Field of the Invention

The invention relates to sensing devices, and aspects thereof, which exploit the unique properties of discotic liquid crystals (DLC).

2. Description of the Related Art

DLCs essentially comprise an aromatic core surrounded by several aliphatic side chains. Typically, a number of aromatic cores are positioned in an aligned, stacked fashion so as to provide for a columnar arrangement. Further, the columns tend to organise into a two dimensional superlattice providing, for example, a hexagonal structure, hexa-alkoxytriphenylenes are well known representatives of this structure of DLCs.

DLCs attracted considerable attention when it was discovered that the columnar phase structure of DLCs was suitable for fast transport of charge carriers. More specifically, it was established that the orientation of the columns directed the flow of this charge because the charge essentially travelled along each column and was further insulated from adjacent columns by the aliphatic side chains attached to the aromatic cores. As a result of this knowledge the use of DLCs in the electronics industry has grown and it is of note that it is the transfer of electric charge along the axis of the columnar DLCs that has been exploited.

However we disclose in this Patent Application a new property of DLCs and a novel way in which this new property can be exploited.

Fluid sensing devices, and in particular gas sensors, are becoming increasingly important for monitoring industrial environments. In particular, they are desirable for use in the chemical industry where the detection of leaks and in particular the detection of leaks of a hazardous nature must be continually monitored. As a result of this various gas sensors have been developed. The most sophisticated is based on polymer technology and essentially involves the interaction of a gaseous molecule with a given polymer and the recording of a response as a result thereof. More specifically, the sensor uses electrically conducting organic polymers based on heterocyclic molecules such as pyrrole. Each polymer is a different functional unit that displays reversible changes in conductivity when it is exposed to polar volatile chemicals. Usually, an array of polymers are provided and the interaction of a gas molecule, or a cocktail of gas molecules, when exposed to each of said polymers in said array is monitored and the subsequent response, or fingerprint, is recorded. Thereafter when the same sensor array is exposed to the same gas, or combination of gases, the same response, or fingerprint, is noted. In this way gas sensors can be "trained" to detect different gases, or combinations of gases, and so be programmed to monitor different, environments for leaks.

However, the aforementioned sophisticated technology is not sufficiently sensitive to detect all kinds of gases and in particular it is not able to detect all organics. Notably, it cannot detect non-polar hydrophobic organics such as benzene and as a result of this its application is not universal.

BRIEF SUMMARY OF THE INVENTION

It is therefore an object of the invention to provide a fluid sensor and in particular a gas sensor which detects a wide range of gases and in particular organic based gases.

It is yet a further object of the invention to provide a sensor and in particular a gas sensor based on the use of DLCs.

It is yet a further object of tie invention to provide a sensor array comprising at least one and preferably a plurality of DLCs and ideally a plurality of differing DLCs.

It is yet a further object of the invention to exploit a new use of DLCs, that being for the detection of fluids and in particular gases and more particularly further still non-polar organic based gases.

It is yet a further object of the invention to provide a sensor that operates in real time.

According to a first aspect of the invention there is therefore provided a fluid sensing device comprising a substrate on which there is provided at least one type of discotic liquid crystal and further wherein there is also provided contact means adapted so as to measure the flow of electric charge through the upper part of the said discotic liquid crystal.

It will therefore be apparent from the above, to those skilled in the art, that we have identified a novel property of DLCs, that being the ability to conduct a surface charge, that is a charge generally perpendicular to the axis of the columns forming the DLCs. Moreover, we have also discovered that this surface conductivity can be affected by fluids and in particular gases such as organic based gases. It therefore follows that the surface conductivity can be used to monitor the levels of, or existence of, fluids and in particular gases in a given environment.

Advantageously the effect on surface conductivity is very fast and so the device is able to operate in real time.

In a preferred embodiment of the invention a plurality of discotic liquid crystals are provided and ideally on a single substrate. Preferably the plurality of discotic liquid crystals are positioned on such substrate so as to provide for an array.

In the preferred embodiment of the invention the response of different discotic liquid crystals to different fluids or gases can be determined, and where an array is provided a given gaseous molecule, or combination of gaseous molecules, can interact with the said array so as to provide a given, typically unique, response. This response can then be recorded and used for future analysis of gases, either identical to the original gas, or gases, or differing therefrom.

Ideally, the said device is also provided with an information storage and retrieval facility whereby data relating to different fluids and in particular gases can be stored and accessed so that analysis of gases or environments can be facilitated.

In yet a further preferred embodiment of the invention said at least one discotic liquid crystal is 2, 3, 6, 7, 10, 11 hexa-hexyloxytriphenylene (HAT6).

More preferably still said discotic liquid crystal comprises at least one such crystal shown in table 1 and exemplified in FIGS. 12 and 13. Ideally said discotic liquid crystal comprises a plurality of the discotic liquid crystal shown in table 1 and exemplified in FIGS. 12 and 13, and ideally each gas sensing device comprises a selected combination of said discotic liquid crystals which combination is selected having regard to the purpose of the sensor. Therefore, for example, where given discotic liquid crystals are shown to be particularly sensitive to a given gas, or combination of gases, then these discotic liquid crystals will be employed in sensors used to detect gases, or combinations of gases, for which they have exemplified favourable sensitivity.

Although the invention has been described with reference to the discotic liquid crystals shown in table 1 and exemplified in FIGS. 12 and 13 it will be understood by those skilled in the art that the invention is not to be limited by the examples of discotic liquid crystals specified in this application, rather the invention lies in the realisation that discotic liquid crystals can be used, because of their surface conductivity, to detect fluids and in particular gases. Thus the number and nature of discotic liquid crystals that can be used in the invention are limitless, as is their combination, selective or otherwise, typically for use in an array.

Surprisingly, we have found that our device responds to different gases whatever the thickness of the DLC layer and we consider this to be because the upper conducting surface remains constant. Indeed, we have found that the thinner the layer the lower the surface resistance and so the greater the conductivity. As a result of this we prefer to use sensors that comprise a relatively thin film of at least one DLC, for example, the said film is typically less than one micrometre and more preferably still less than 0.5 of a micrometer and ideally in the order of 0.1 micrometers.

According to a second aspect of the invention there is provided a sensor array, for use in a fluid sensor, comprising at least one type of discotic liquid crystal.

In a preferred embodiment of the second aspect of the invention a plurality of different discotic liquid crystals are used. More preferably still means are provided to measure surface current flow across each type of discotic liquid crystal.

According to a yet third aspect of the invention there is provided the use of at least one discotic liquid crystal for use in detecting a fluid and in particular a gas, especially an organic based gas such as a non-polar gas.

Whilst we would not intend for the invention to be limited by the following explanation, we consider that discotic liquid crystals function as fluid, and in particular gas, sensors because of the ability of the aliphatic side chains to interact with said gases and so affect the organisation at the surface of the discotic liquid crystal structure. The enhancement or depression of surface organisation thus affects the ability of the surface to conduct charge and we speculate, that in this way, a given fluid interacts with the surface of a discotic liquid crystal to affect surface organisation and thus charge flow therethrough.

We believe that DLCs will be especially useful for sensing non-polar hydrophobic volatile chemicals in vapour sensing instruments usually referred to as "the electronic nose". These instruments, which detect smell levels down to parts per billion normally use an array of 8, 16 or 32 separate gas sensors. It is thought that DLCs may be used in such sensors and exploited because of the ability of DLCs to detect non-polar hydrophobic gases.

An embodiment of the invention will now be described by way of example only with reference to the following Figures wherein:

Figure 13:
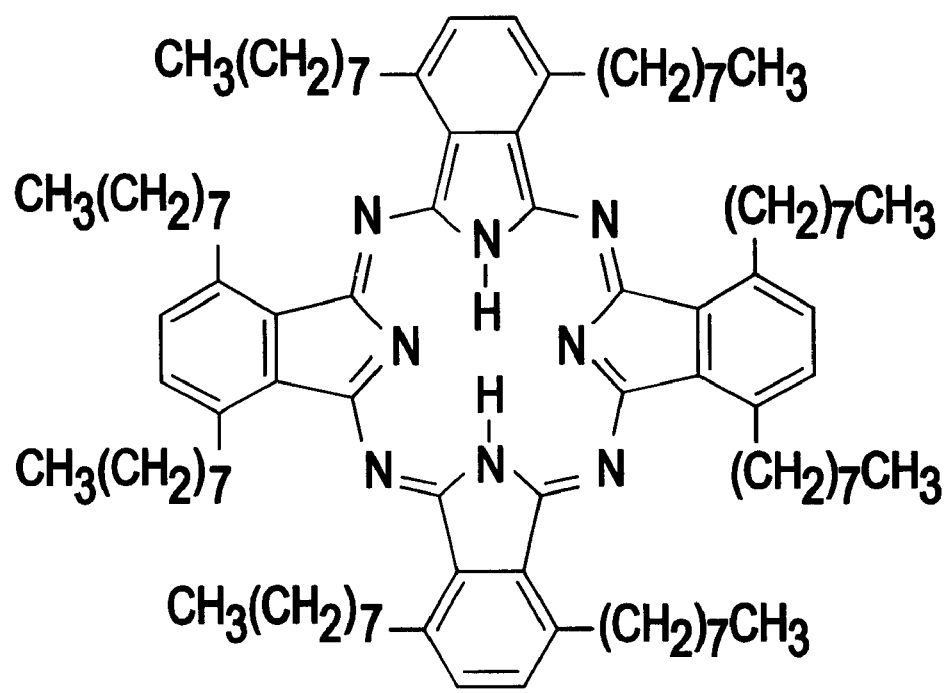

Table 1 is a list of discotic liquid crystals suitable for working the invention;

FIGS. 12 and 13 show the chemical structure of the discotic liquid crystals referred to in table 1.

FIG. 14 is a list of discotic liquid crystals suitable for working the invention.

DETAILED DESCRIPTION OF THE INVENTION

Figure 1:
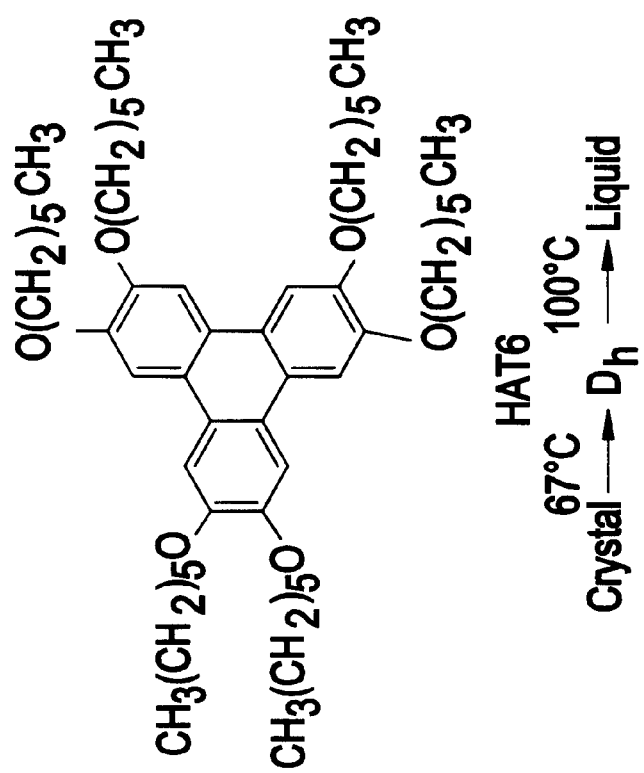
FIG. 1 shows the chemical structure of a selected discotic liquid crystal.

Referring to the Figures and firstly to FIG. 1, there is shown the chemical structure of a selected discotic liquid crystal HAT6. It can be seen that the structure comprises an aromatic core surrounded by a number of aliphatic side chains. HAT6 exists in a crystalline phase below 67° C. and is transformed into a liquid phase at temperatures in the order of 100° C.

The basis structure shown in FIG. 1 is typical of all discotic liquid crystals in that they essentially comprise an aromatic core surrounded by a number of aliphatic side chains. Moreover, the liquid crystalline state is located between a crystalline and isotropic liquid state.

Figure 2:
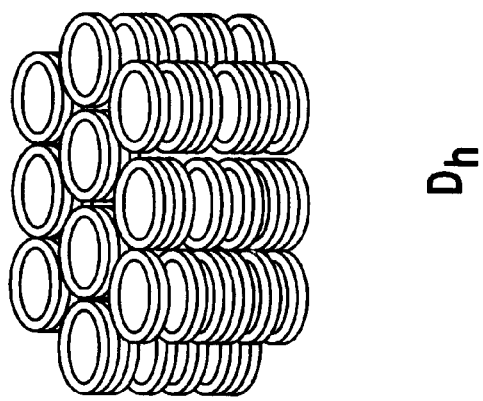
FIG. 2 is a diagrammatic representation of the organisational structure of a discotic liquid crystal.

In FIG. 2 there is shown the organisational arrangement of a film of discotic liquid crystals. Essentially, the aromatic cores are aligned and stacked so as to form columnar arrangements, thus the aliphatic side chains are provided between the aromatic columns and so act as spacers.

Furthermore, they also act as insulators so ensuring that, in conventional applications, electric charge transfer is directed along the longitudinal axis of the columns.

Discotic liquid crystals are known to have a number of favourable properties, one being their wetting property and thus the ability to ensure efficient molecular contact with electrodes and the other being the high degree of internal order which occurs with the semi-fluidity of discotic liquid crystals. The former property is advantageous in terms of construction of devices using discotic liquid crystals and the latter property is advantageous in that it provides for "self-healing" if a disturbance should occur at the molecular level.

Figure 3:
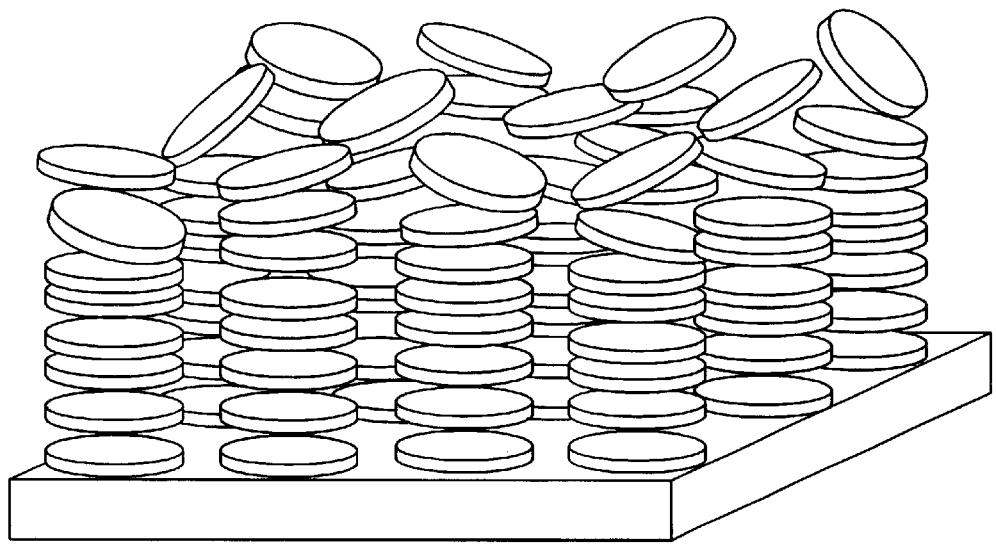
FIG. 3 is a diagrammatic representation of a discotic liquid crystal film on a substrate.

FIG. 3 shows the arrangement of discotic liquid crystals on a substrate. It can be seen that the organisation of the columnar structure tends to break down towards the surface and indeed it is this property which we exploit in this invention. However, we have found that despite the thickness of the discotic liquid crystal film the surface conductivity remains and therefore we conclude that whatever the thickness of the film the advantageous surface structure remains. Indeed, data to be presented hereinafter will show that thin films of discotic liquid crystals are preferred.

Figure 4:
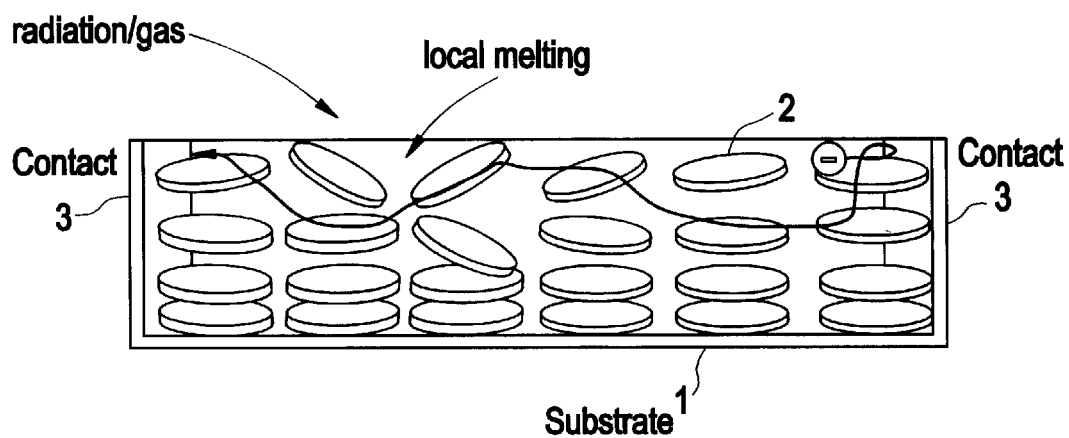
FIG. 4 is a diagrammatic illustration of a fluid sensor in accordance with the invention.

In FIG. 4 we show a sensing device in accordance with the invention. The device essentially comprises a substrate 1 on which there has been deposited at least one discotic liquid crystal 2 existing in the liquid-crystalline state and so displaying the organised structure typical of its type.

Positioned at selected locations, that is on either side of the discotic liquid crystal's surface, and so in opposing fashion, are a pair of contact means 3 such as electrodes. As aforementioned, the wetting properties of the discotic liquid crystal ensures that once the DLCs film is applied to the substrate and then placed in contact with the contact means good electrical contact is provided. Ideally the contact means comprise a pair of electrodes to which a voltage can be applied so ensuring that current can flow.

As previously hypothesised exposure of the device, and in particular discotic liquid crystals to a fluid and ideally a gas results in interaction of the gas with the discotic liquid crystal and in particular the surface of the discotic liquid crystal so as to affect the surface conductivity of the discotic liquid crystal. Various gases react differently with the discotic liquid crystal in order to provide for variable current flows. In this way each gas provides a variable current which can be used, either in isolation or in combination with other such readings using different discotic liquid crystals, to identify it.

In copending unpublished GB patent application number 9608774.7 is described for example a method for analysing the unique signature obtained in the form of a response as a function of frequency.

The sensing device may therefore be of such diverse applications as: process control, by monitoring organic chemical reactions in real time; environmental monitoring, by early detection of contamination; hazard detection, by rapid indication of the presence of hazard gases and the like.

Test Data

In the following tests the device shown in FIG. 4 was employed using the discotic liquid crystal shown in FIG. 1. However, it is within the scope of the invention to employ the use of any one or more of the discotic liquid crystals shown in table 1, and corresponding FIGS. 12 and 13, and indeed the selection of a single, or combination of, discotic liquid crystal (s) will be discussed hereinafter.

In addition to the discotic liquid crystals specifically described herein it is also envisaged that discotic liquid crystals having modified aliphatic side chains may also be used. In particular, discotic liquid crystals having side chains which are engineered so as to be relatively, hydrophobic, hydrophilic, long in length, short in length, high in dipole moment, low in dipole moment or otherwise may be used.

Figure 5:
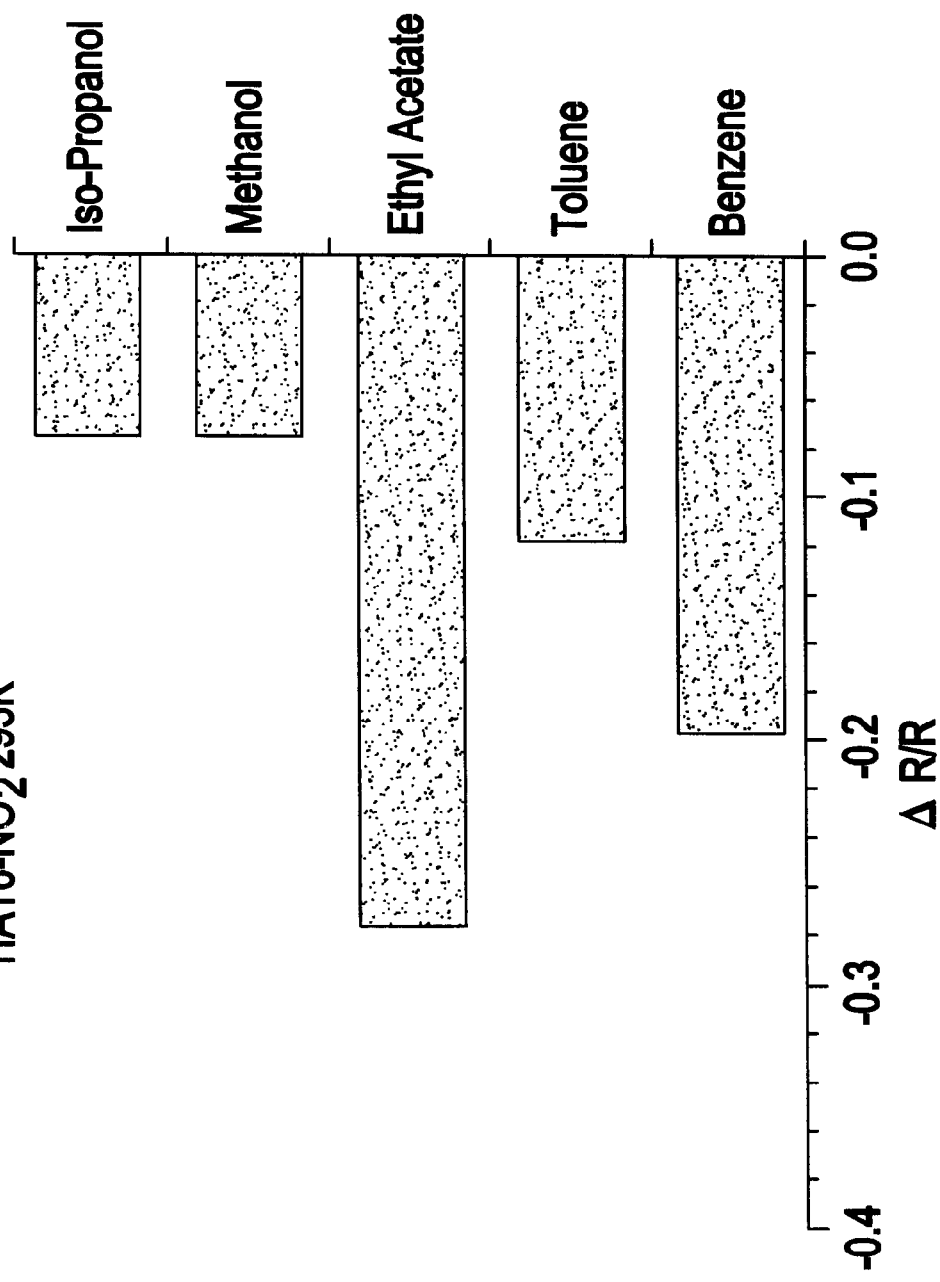
FIG. 5 is a graph showing a measure of resistance, and so conductivity, of a selected discotic liquid crystal surface, in response to a variety of organics.

Referring therefore to FIG. 5 it can be seen that the sensor of the invention was able to distinguish between acetates such as Ethyl Acetate and ring structures such as Benzene and Toluene.

Figure 6:
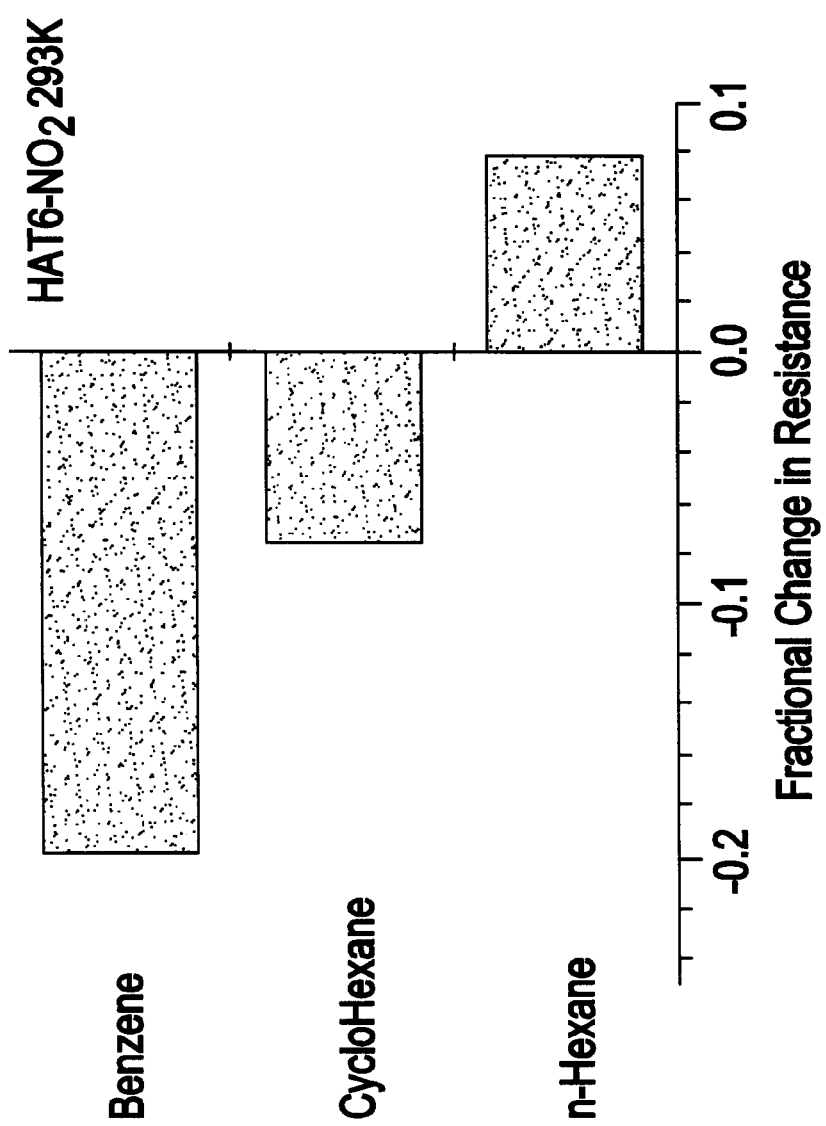
FIG. 6 is a graph showing a measure of resistance, and so conductivity of a selected discotic liquid crystal surface in response to aromatic and aliphatic hydrocarbons.

FIG. 6 shows that the sensor of the invention was also able to distinguish between aromatics and aliphatics and moreover that this ability to distinguish is polarised such that a ring structure such as Benzene or CycloHexane provides for a reduction in resistance, and so an increase in current flow, whereas an aliphatic such as n-Hexane provides for an increase in resistance and so a reduction in current flow.

Figure 7:
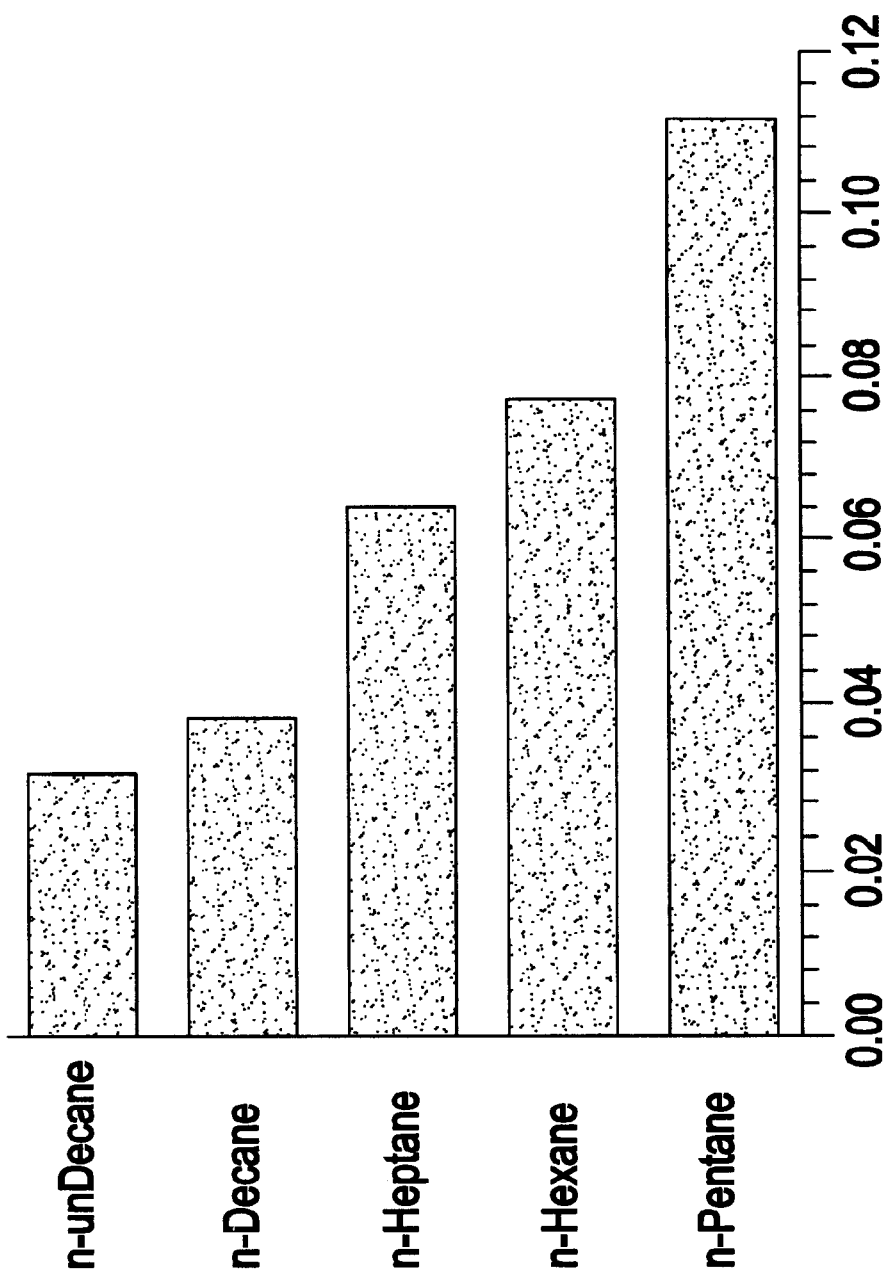
FIG. 7 is a graph showing a measure of resistance, and so conductivity of a selected discotic liquid crystal surface, in response to aliphatic hydrocarbons of varying chain lengths.
Figure 10:
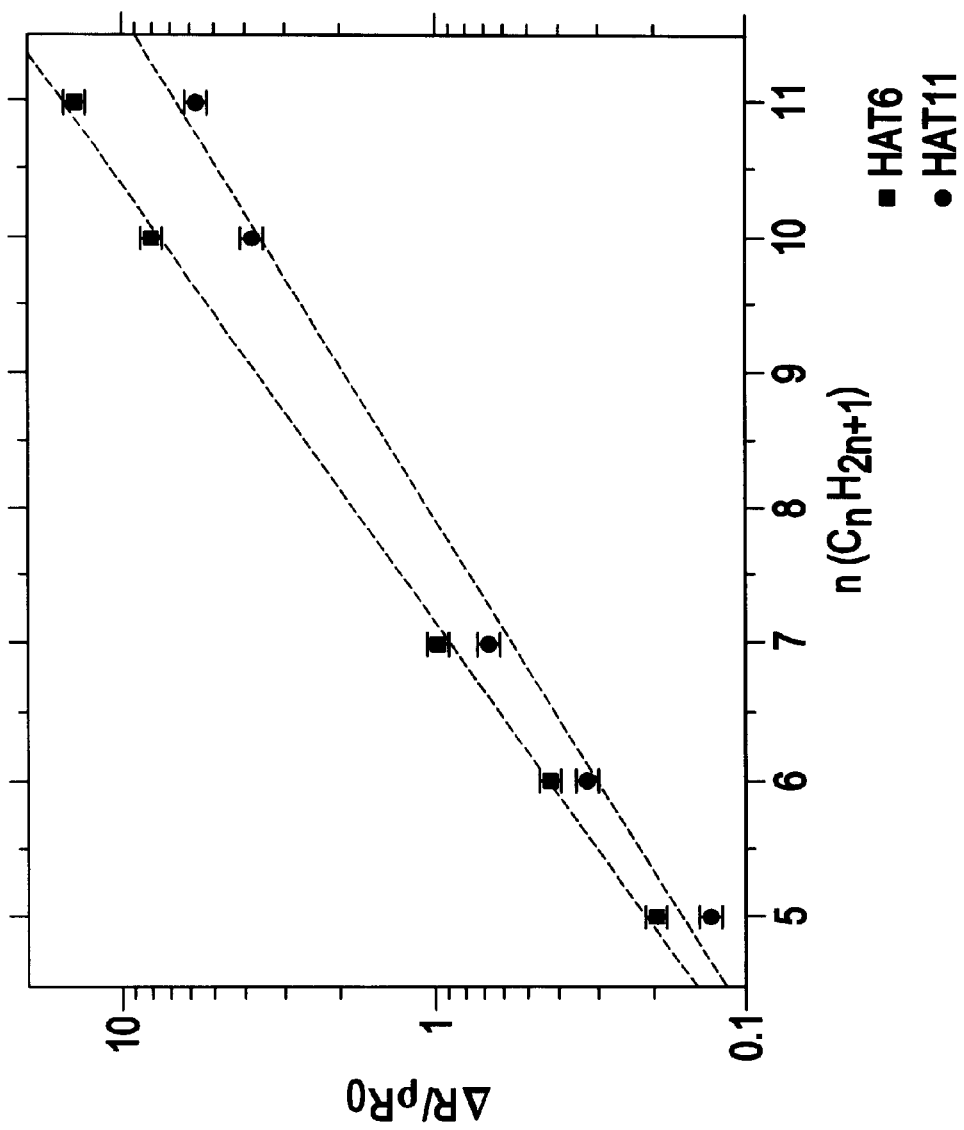
FIG. 10 is a graph showing how the increasing length of carbon chains affects the resistance, and so conductivity, of the surface of a selected discotic liquid crystal having compensated for the partial pressure of the gas.

In FIG. 7 it can be seen that the device of the invention can be used to distinguish between different aliphatics and in particular the chain length of different alipliatics. Summarily, the greater the carbon chain length the lower the resistance and so the greater the conductivity. This is further also shown in FIG. 10 where it can be seen that there is a linear relationship between resistance at the discotic liquid crystal surface and chain length.

Figure 8:
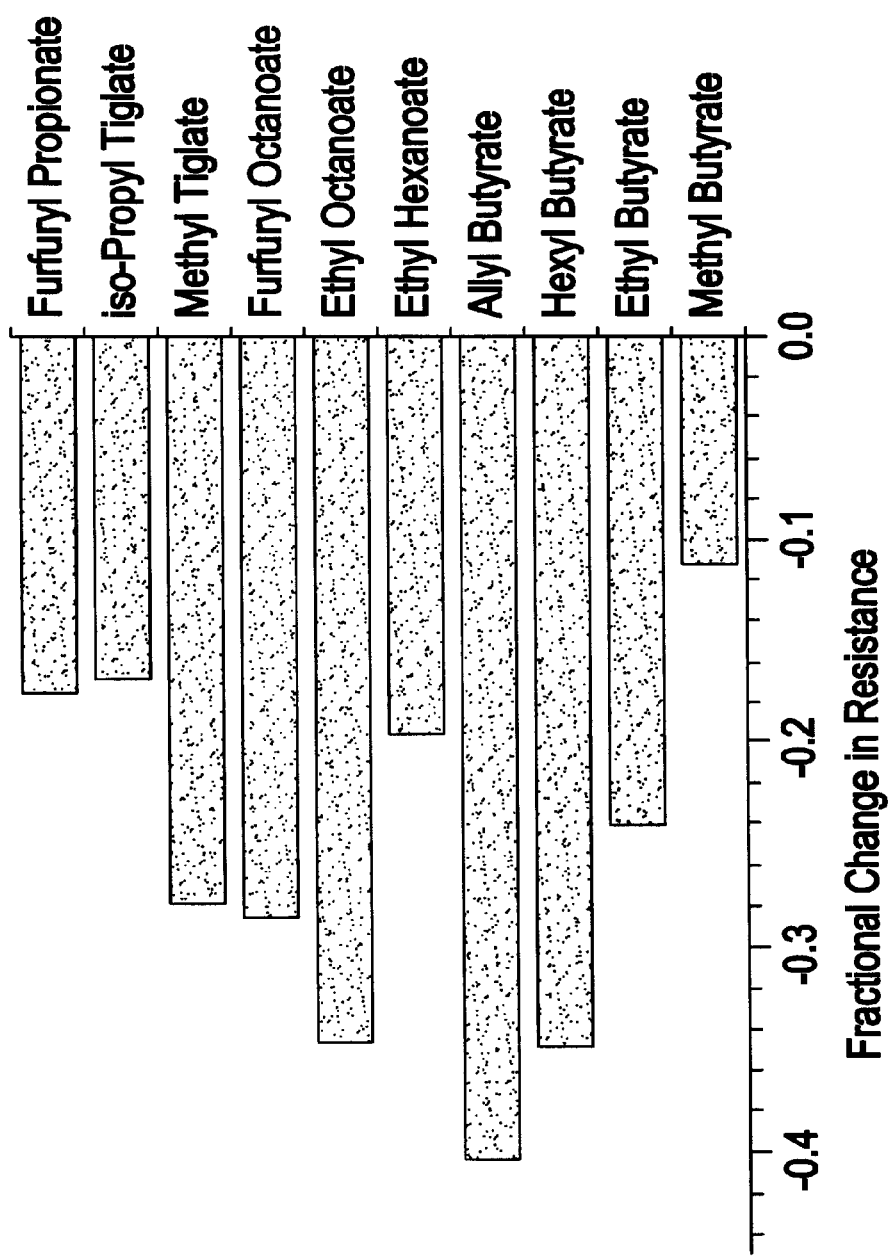
FIG. 8 is a graph showing a measure of resistance, and so conductivity of a selected discotic liquid crystal surface, in response to various esters.
Figure 9:
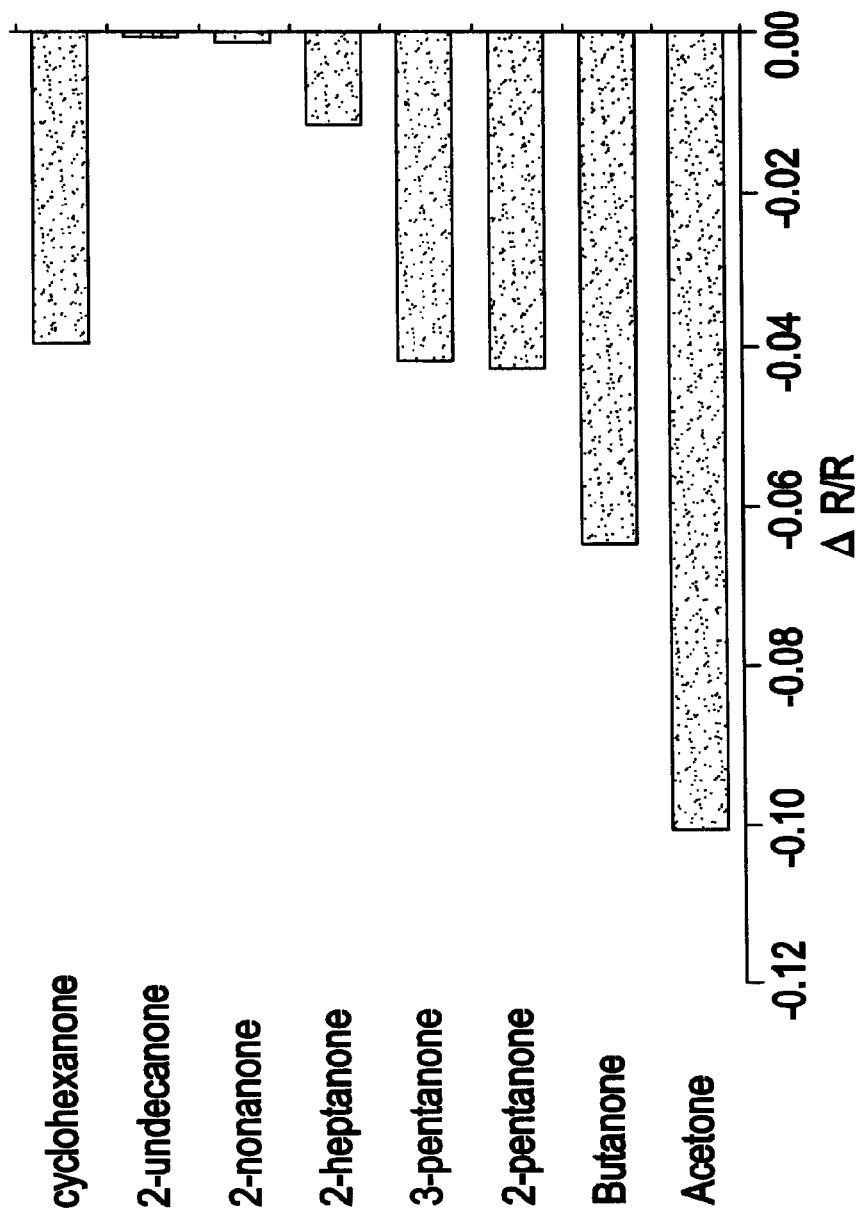
FIG. 9 is a graph showing a measure of resistance, and so conductivity of a selected discotic liquid crystal surface in response to various ketones.

In FIGS. 8 and 9 it can be seen that the device of the invention can distinguish between different esters and ketones, respectively, and so has a wide range of application.

It is thought that prior art devices are able to detect those organics shown in FIG. 9 but are unable to detect those organics shown in FIG. 8. It is therefore apparent that this invention is able to detect both types of gases and therefore can be used to detect either non-polar gases i.e. those shown in FIG. 8 which are currently undetectable using prior art devices, or a mixture of polar and non-polar gases.

All of the aforementioned results illustrate the sensitivity of discotic liquid crystals in detecting different gases and in particular organic based gases.

In a preferred embodiment of the invention, not shown, we prefer to use a device comprising an array of selected discotic liquid crystals wherein the surface current flow for each of said selected discotic liquid crystal in said array can be measured. Typically, the discotic liquid crystals selected for use in the array are chosen on the basis of their sensitivity to particular fluids. In this way devices can be customised according to a users requirements. Alternatively, where the purpose of the device is unknown a plurality of discotic liquid crystals can be selected on the basis of the range of fluids that can be detected. Ideally any one or more of the discotic liquid crystals shown in table 1 and exemplified in FIGS. 12 and 13 are used. However, it is not intended that this invention should be limited to the specific discotic liquid crystals specified herein, rather the invention may employ any one or more known discotic liquid crystal(s).

Figure 11:
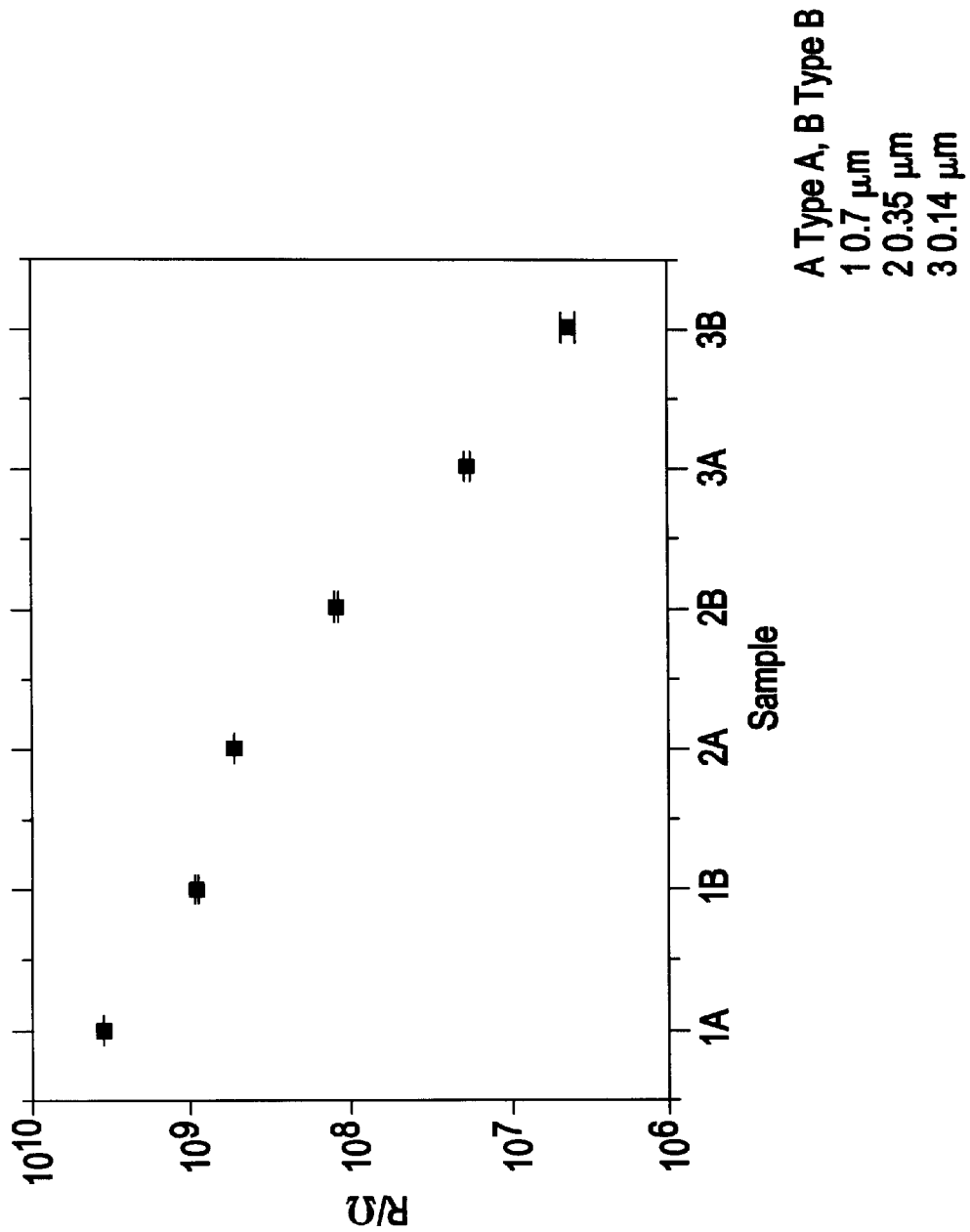
FIG. 11 is a graph showing a measure of resistance, and so conductivity of a selected discotic liquid crystal surface, in response to discotic liquid crystal film thickness.

In working the invention we have discovered that the conductivity at the surface, and across the surface of the discotic liquid crystal arrangement, remains despite the thickness of the discotic liquid crystal film. Indeed, we have surprisingly found that as the film thickness decreases the surface resistance decreases and so the surface conductivity increases, see FIG. 11. As a result of this we prefer to use devices which include a thin film of at least one discotic liquid crystal. Ideally we prefer devices which include at least one film that is less than one micrometre. Ideally further still we prefer to use films that are less than 0.5 micrometers and ideally in the order of 0.1 micrometer.

The provision of such a thin film is effected using the following method.

A solution of known composition is made up by dissolving the required weight of discotic liquid crystals in a low boiling point solvent (such as diethylether or carbon disulphide). Thin films are then formed on the electrode surface by casting a known volume of solution followed by evaporation of solvent. Homeotropic alignment of the thin film is achieved by suitable heat treatment which consists of heating the film to a temperature above its clearing point into the isotropic phase, followed by a slow cooling into the liquid crystalline phase.

Thus we describe herein the use of discotic liquid crystals to detect fluids and in particular gases by measuring the surface discotic liquid charge associated with the interaction of said fluid and said discotic liquid crystal.

What is the claimed is:

1. A fluid sensing device comprising a substrate on which at least one type of a discotic liquid crystal (DLC) comprising a film having a thickness of less than one micrometer is arranged to form an array of columnar structures, said array of columnar structures having an upper part adapted for interaction with a fluid to be sensed, contact means comprising a plurality electrodes which are positioned on opposing sides of said array of columnar structures so that an electric charge applied to at least one electrode flows generally across a surface of the upper part of said array of columnar structures in a direction substantially perpendicular to a vertical axis of said columnar structures, wherein said fluid sensing device measures a change in the flow of electric charge caused by a change in surface conductivity across the surface of the upper part of said array of columnar structures, said change representing the interaction of said fluid to be sensed with the surface of the upper part of said array of columnar structures.

2. A fluid sensing device according to claim 1, which provides fluid sensing in real time according to a change in the flow of electric charge measured by said contact means across the surface of the upper part of said array of columnar structures.

3. A fluid sensing device according to claim 1, further comprising means for information retrieval of data relating to the interaction of various fluids and gases with said at least one type of discotic liquid crystal.

4. A fluid sensing device according to claim 3, wherein the retrieved data includes information regarding the interactions of combinations of said various fluids and gases with said at least one type of liquid crystal.

5. A fluid sensing device according to claim 1, wherein said at least one discotic liquid crystal is selected from the group consisting of 1–6 β-triphenylenes and tricycloquinazolines, 1–6 α-triphenylenes and tricycloquinazolines, and substituted phthalocyanines.

6. A fluid sensing device according to claim 5, which comprises at least one discotic liquid crystal is selected from the group consisting of 2,3,6,7,10,11-Hexa(hexyloxy) triphenylene (HAT 6); 1-Nitro 2,3,6,7,10,11-Hexa (hexyloxy)triphenylene (HAT6-NO$_2$); 2,3,7,8,12,13-Hexa-(2-(2'-MethoxyEthoxy)-Ethoxyl)TriCylcoQuinazoline (HMEETCQ); and 1,4,8,11,15,18,22,25-Octa-(Octyl) Phthalocyanine (PC8).

7. A fluid sensing device according to claim 1, wherein said at least one discotic liquid crystal has side chains which are selected from the group consisting of hydrophobic, hydrophilic, high in dipole movement, and low in dipole movement.

8. A fluid sensing device according to claim 1, wherein said at least one type of discotic liquid crystal comprises a combination of discotic liquid crystals selected on the basis of at least one of sensitivity to particular fluids to be sensed by said fluid sensing device, and sensitivity to a range of particular fluids to be sensed by said fluid sensing device.

9. A fluid sensing device according to claim 8, wherein at least one type of discotic liquid crystal of said combination of discotic liquid crystals comprises 2,3,6,7,10,11, hexa (hexyloxy) triphenylene (HAT6).

10. A fluid sensing device according to claim 1, wherein said film of said at least one type of discotic liquid crystal has a thickness of less than 0.5 micrometers.

11. A fluid sensing device according to claim 10, wherein said film has a thickness less than 0.1 micrometers.

12. A method for detecting a fluid comprising the steps of:
exposing a sensing device as defined in claim 1 to a fluid so that said fluid interacts with the surface of at least one discotic liquid crystal, applying a voltage to the contact means, measuring a flow of electric charge between the contact means, and analyzing a variation in flow of electric charge to identify the fluid.

13. A method according to claim 12, wherein said analyzing step includes comparing the variation in flow of electric charge for a particular discotic liquid crystal with values in an information storage means.

14. A sensor array for a fluid sensing device, comprising a plurality of discotic liquid crystals having a thickness of less than one micrometer on a substrate, and means for measuring a surface current flow across a surface of said discotic liquid crystals.

15. A method for the preparation of a fluid sensing device comprising the steps of:

(a) providing a film of at least one type of discotic liquid crystal having a thickness of less than one micrometer on a substrate, (b) providing contact means adapted for measuring a flow of electric charge across an upper part of the film of said at least one type of discotic liquid crystal.

16. A method according to claim 15, wherein step (a) includes aligning the thin film planarly on the substrate. contact means.

17. A method according to claim 16, wherein said substrate comprises an electrode surface in contact with said contact means.

18. A method according to claim 15, wherein said substrate comprises an electrode surface in contact with said contact means.

* * * * *